United States Patent [19]
Engelhardt et al.

[11] Patent Number: 5,726,331
[45] Date of Patent: Mar. 10, 1998

[54] DIMETHYL N-LAUROYL-L-GLUTAMATE

[75] Inventors: Fritz Engelhardt, Chesapeake, Va.; Manfred Müller, Gelnhausen; Michael Wessling, Maintal-Bischofsheim, both of Germany

[73] Assignee: Hoechst Aktiengesellschaft, Frankfurt, Germany

[21] Appl. No.: 751,407

[22] Filed: Nov. 21, 1996

[30] Foreign Application Priority Data

Nov. 24, 1995 [DE] Germany ............... 195 43 792.6

[51] Int. Cl.$^6$ .................................. C07C 231/00
[52] U.S. Cl. ............................ 554/36; 554/30
[58] Field of Search ............................ 554/36

[56] References Cited

FOREIGN PATENT DOCUMENTS 60-105645  6/1985  Japan.
62-048648  3/1987  Japan.

OTHER PUBLICATIONS

Jain, J.C. et al. "A New Approach For Esterification of Amino Acids", Indian Journal of Chemistry, Section B, Bd. 15, Nr. 8, 1977, pp. 766–767.

Springer–Verlag, Berlin, Göttingen Heidelberg, DE, "Beilsteins Handbuch der Organischen Chemie, veirte Auflage, drittes Erganzungswerk", Bd. 4, Teil 2, pp. 1545, 1963.

Patent Abstracts of Japan, vol. 9, No. 247 (C–307), Oct. 3, 1985.

Patent Abstracts of Japan, vol. 11, No. 242 (C–438) Aug. 7, 1987.

*Primary Examiner*—Paul J. Killos
*Attorney, Agent, or Firm*—Connolly and Hutz

[57] ABSTRACT

The present invention relates to a process for the preparation of dimethyl N-lauroyl-L-glutamate by reaction of N-lauroyl-L-glutamic acid with methanol in the presence of trimethyl orthoformate.

4 Claims, No Drawings

DIMETHYL N-LAUROYL-L-GLUTAMATE

The present invention relates to a process for the preparation of dimethyl N-lauroyl-L-glutamate by reaction of N-lauroyl-L-glutamic acid with methanol in the presence of trimethyl orthoformate.

N-Lauroyl-L-glutamic acid bis-n-butylamide is a raw material for the cosmetics industry, for whose preparation pure dimethyl lauroyl-L-glutamate is needed. However, to date there is no process available which yields this ester in pure form in an efficient manner. For the preparation of carboxylic acid esters and dicarboxylic acid diesters, there are a multiplicity of synthetic routes adequately cited in the literature. It is possible here to convert all types of functional groups into ester functions. Thus the synthesis of esters is carried out by reaction of activated carboxylic acid derivatives such as, for example, acid chlorides or acid anhydrides with alcohols, usually in very good to quantitative yields. On the other hand, if the direct esterification of carboxylic acids with alcohols is looked at, what is concerned is a typical equilibrium reaction. The shift of the equilibrium in favor of the products takes place, as is known, as a result of the use of one of the reactants in excess. In order to make the yields as quantitative as possible, it is necessary in most cases—i.e. even in the reaction of N-lauroyl-L-glutamic acid with methanol—additionally to remove one of the reaction products, usually the water of reaction formed, from the equilibrium. To this end, entraining agents are generally employed which make it possible to distil off the water of reaction azeotropically. If the ester of an alcohol which forms an azeotrope with water is desired, this can be employed as the agent of choice.

Since methanol does not form an azeotrope with water, the last-mentioned possibility for shifting the equilibrium is eliminated. The reaction of N-lauroyl-L-glutamic acid (LGA) in an excess in methanol (5–10 mol of MeOH/mol of LGA) leads after a relatively long reaction time (8–10 hours) only to a conversion of about 50–60% (HPLC). Even a doubling of the reaction time does not lead to any noticeable improvement in the conversion.

Surprisingly, it has now been found that the reaction of LGA to give dimethyl N-lauroyl-L-glutamate proceeds virtually quantitatively within very short reaction times if the reaction is carried out in the presence of trimethyl orthoformate with acid catalysis.

The present invention accordingly relates to a process for the preparation of dimethyl N-lauroyl-L-glutamate by reaction of N-lauroyl-L-glutamic acid with methanol, which comprises carrying out the reaction in the presence of trimethyl orthoformate with acid catalysis.

Preferably, in the process according to the invention 1 to 10 mol of methanol and 0.01 to 0.2 mol of the catalyst are employed per mole of LGA. Particularly preferably, 1.5 to 3 mol of methanol and 0.03 to 0.08 mol of catalyst particularly preferably per mole of LGA.

The acid catalyst employed is preferably p-toluenesulfonic acid, it also being possible, however, to use all other acids customary for this purpose.

In the process according to the invention, the trimethyl orthoformate reacts with the water liberated in the esterification to give methyl formate and methanol. In a preferred embodiment of the process according to the invention, the methyl formate, which boils at 31°–32° C., is removed from the reaction mixture by distillation at the time of its formation, while the methanol formed is additionally used for the esterification of the N-lauroyl-L-glutamic acid.

The process according to the invention proceeds smoothly and leads in 3 to 5 hours to the desired product in virtually quantitative yield and high purity after distillative removal of the excess of methanol.

The starting substances needed for the process according to the invention are all known and commercially available.

EXAMPLES

Example 1

1000 g (3.034 mol) of LGA are introduced into 200 g (6.242 mol) of methanol in a 2 l-four-necked flask having a thermometer, KPG stirrer, dropping funnel and temperature-controllable column with an attached Claisen bridge and, after addition of 20 g (0.116 mol) of p-toluenesulfonic acid, the mixture is heated to reflux (71° C.). Over a period of 3.5 h, 670 g (6.314 mol) of trimethyl orthoformate are then added dropwise. As soon as the first drops are added, increased reflux commences in the column, which is temperature-controlled at 39° C., and after a short time methyl formate begins to distill off at the top (31°–36° C.). After addition of the orthoester, the mixture is heated to reflux for a further 30 min, the flow of distillate decreasing to zero. The amount of distillate corresponds to theory (about 380 g,~6.1 mol of methyl formate+methanol additionally carried over). The excess of methanol is distilled off at normal pressure, then remains of orthoester are distilled off in vacuo and after cooling a largely colorless melt is obtained. The progress of the reaction can be monitored by thin-layer chromatography (product: only one spot). After comminution, the melt yields a colorless powder of melting point 62°–63° C.

Yield: 1099.2 g (>98%) of dimethyl N-lauroyl-L-glutamate

Purity: Pure by TLC, starting spot p-TosOH HPLC (area %) >98%

Hydrolysis number: 313 mg of KOH/g of substance (theory: 314 mg of KOH/g)

Example 2 (comparison)

100 g (0.303 mol) of LGA are introduced into 97.2 g (3.034 mol) of methanol in a 1 l-four-necked flask having a thermometer, KPG stirrer and reflux condenser and, after addition of 10.32 g (0.060 mol) of p-toluenesulfonic acid, the mixture is heated to reflux for 8 h (66°–67° C.). The excess of methanol is distilled off at normal pressure, then residual MeOH and the water still present are distilled off in vacuo and a yellowish cloudy melt is obtained, which on cooling solidifies to give a yellowish crystalline mass. The progress of the reaction can be monitored by thin-layer chromatography (product: several spots, LGA starting material clearly present).

Yield: 116 g

Purity: about 60% dimethyl N-lauroyl-L-glutamate (HPLC, area %).

We claim:

1. A process for the preparation of dimethyl N-lauroyl-L-glutamate by reaction of N-lauroyl-L-glutamic acid with methanol, which comprises carrying out the reaction in the presence of trimethyl orthoformate with acid catalysis.

2. The process as claimed in claim 1, wherein the acid catalyst used is p-toluenesulfonic acid.

3. The process as claimed in claim 1, wherein resultant methyl formate is removed from the reaction mixture by distillation.

4. The process as claimed in claim 1, wherein the methanol formed from trimethyl orthoformate is additionally used for the esterification of N-lauroyl-L-glutamic acid.

* * * * *